United States Patent [19]
Lomasney

[11] Patent Number: 5,543,719
[45] Date of Patent: Aug. 6, 1996

[54] BARRIER LEAK DETECTION USING ELECTROKINETIC ION TRANSPORT

[75] Inventor: Henry L. Lomasney, New Orleans, La.

[73] Assignee: Ionex Corporation, New Orleans, La.

[21] Appl. No.: 282,268

[22] Filed: Jul. 29, 1994

[51] Int. Cl.[6] .......................... G01N 27/00; G01N 27/20
[52] U.S. Cl. .......................... 324/557; 324/326; 324/718; 73/40; 340/605
[58] Field of Search .................... 324/551, 554, 324/557–559, 713, 715, 718, 326, 237, 238, 239, 240; 73/40, 49.2; 340/604, 605, 606

[56] References Cited

U.S. PATENT DOCUMENTS

| | | | |
|---|---|---|---|
| 4,639,669 | 1/1987 | Howard et al. | 73/597 X |
| 4,740,757 | 4/1988 | Converse et al. | 324/557 X |
| 4,947,470 | 8/1990 | Darilek | 324/557 |
| 5,214,387 | 5/1993 | Fenner | 324/577 |

FOREIGN PATENT DOCUMENTS

| | | | |
|---|---|---|---|
| 3701130 | 7/1988 | Germany | 324/559 |

*Primary Examiner*—Kenneth A. Wieder
*Assistant Examiner*—Diep Do
*Attorney, Agent, or Firm*—Foley & Lardner

[57] ABSTRACT

Procedures and apparatuses for determining the integrity of a geophysical barrier are provided. In particular, an electropotential gradient is established across the barrier in an attempt to drive ionic species through the barrier. The resulting ionic transport results in a current which can be measured between the electrodes, and which can be correlated to the integrity of the barrier. The location of a leak in the barrier can be determined by the use of an electromagnetic sensor which detects an anomaly in the flux field associated with the current.

10 Claims, 1 Drawing Sheet

BARRIER LEAK DETECTION USING ELECTROKINETIC ION TRANSPORT

FIELD OF THE INVENTION

The present invention relates to processes and apparatus for determining the integrity of a geophysical barrier. In particular, an electropotential is established across the barrier for the purpose of driving (or attempting to drive) ions across the barrier. This ion migration results in a current, which can be measured and correlated to the integrity of the barrier.

BACKGROUND OF THE INVENTION

There are numerous types of barriers used to confine hazardous materials and toxic waste in order to prevent environmental damage to the surrounding areas. Leakage of ions and minerals via aqueous diffusion transport through such barriers is unacceptable from an environmental viewpoint.

In recent years, the technology of geophysical barriers has been advanced through use of various ion impermeable materials such as cementitious grouts, polymer barriers, clay barriers, and ice walls. The performance of such engineered barriers has heretofore been measured using monitoring wells. Such an approach is limited inasmuch as the location of a leakage zone is not easily pinpointed and the quantification of the leak is limited, especially in a short term study.

Recently, it has been recognized that the streaming potential can be used to map the flow of liquid in, for example, geophysical strata. In another application of electrical conductivity detection, a sensor system has been developed for use with sheet polymer lined waste disposal and treatment ponds, industrial surface impoundments, basins, and similar containment designs.

This system detects the anomalies in the current density which is the basis for identifying breaches in liners, pipelines and other containment systems holding liquid chemical wastes. Basic electrical parameters (voltage and current) are used to indicate the location of the anomaly. The detection system utilizes five components—a passive sensor, an active current electrode, a monitoring center, connecting cables, and a data acquisition station. In this adaptation, the localized water flow and resultant electrical current carrying anomaly is accomplished by means of migration of soluble ions through the soil/water composite.

In general, this system requires that an impoundment be flooded in order to detect a leak and to permit electrical "coupling" of the passive electrode and the sensing electrode. Furthermore, the flooded pond is necessary in order to provide the leakage of liquid into the soil which in turn presents the electrical resistance anomaly. Thus, this system has limited applications.

There is a need, therefore, for a process for determining the integrity of a geophysical barrier that permits the quantification and localization of any leaks, and that does not require a flooded impoundment system.

SUMMARY OF THE INVENTION

It is therefore an object of the present invention to provide a process and apparatus for determining the integrity of a geophysical barrier. It is a further object of the present invention to provide a process and apparatus for determining the location of a leak in a geophysical barrier.

In accomplishing these objects, the invention provides a process for determining the integrity of a geophysical barrier comprising the steps of providing an electrode pair positioned on opposite sides of the barrier, establishing an electropotential across the electrode pair, and measuring the resultant current caused by said electropotential. The location of the leak can be determined by additionally using an electromagnetic sensor to measure an electromagnetic field. Apparatus for performing these processes are also provided.

In another advantageous embodiment, a leaking barrier may be further characterized and quantified through the use of a pulsed power delivery system and the capacitance and inductance properties of the confined materials.

Yet another aspect of the present invention provides a data acquisition system and mathematical model for acquiring current and voltage data over a long time interval and subsequently analyzing the data to precisely determine the functional integrity of the geophysical barrier.

Additional objects and advantages of the invention will be set forth in part in the description that follows, and in part will be obvious from the description, or may be learned by practice of the invention. The objects and the advantages of this invention may be realized and obtained by means of the processes and apparatuses particularly pointed out in the appended claims.

DETAILED DESCRIPTION OF THE PREFFERED EMBODIMENTS

Figure 1:
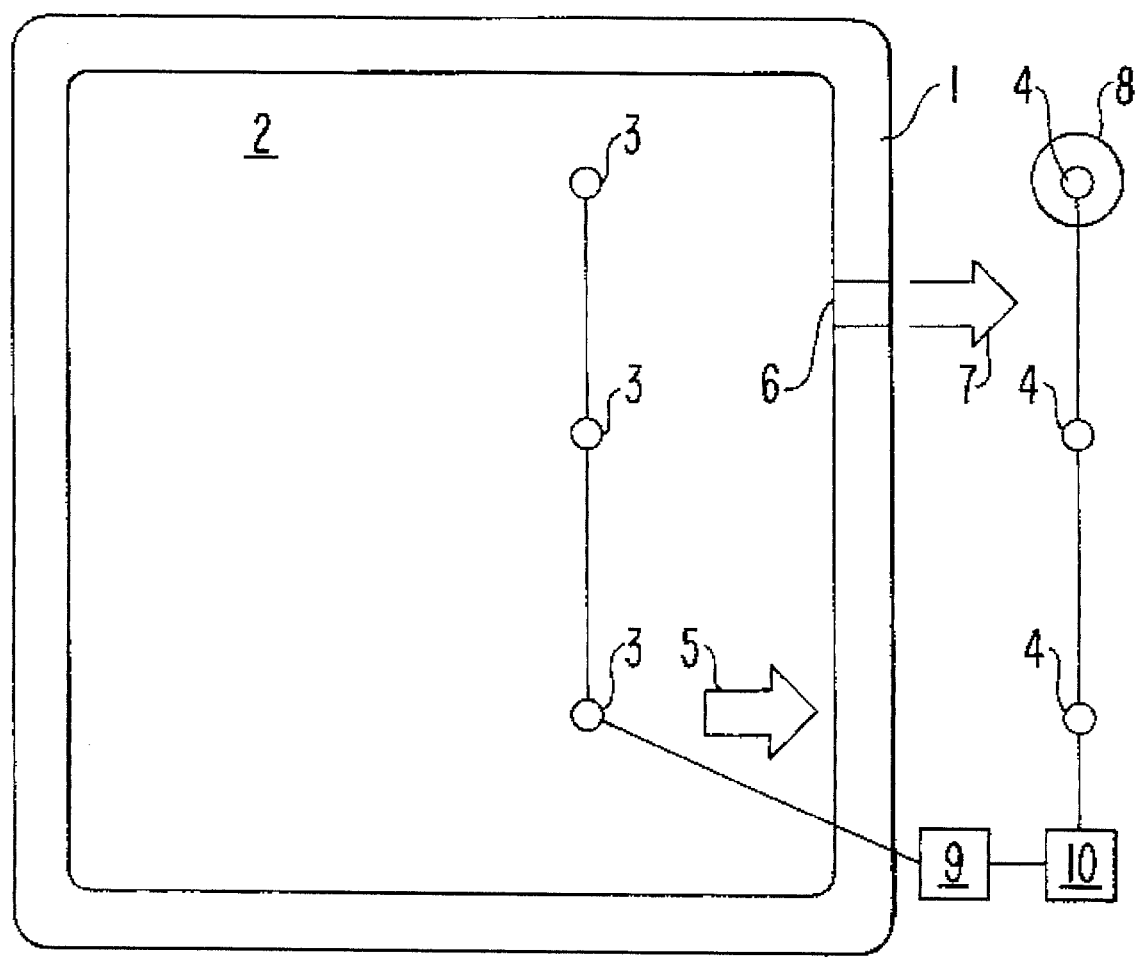
FIG. 1 is a schematic drawing of an apparatus in accordance with this invention.

The present invention provides a method for determining the integrity of a geophysical barrier and for identifying the location and size of any breach therein which would permit ion migration through the barrier. In basic terms, the process of this invention generally involves (i) establishing an electropotential on ions within the barrier to drive (or attempt to drive) them through the barrier, thus establishing a substantial ionic flux (current), and (ii) using an electromagnetic sensing device to detect any anomaly in the ionic flux pattern of the current.

More specifically, the processes and apparatus of this invention generally use an electrode array which is in electrochemical contact with the barrier. In general, soluble ions are responsible for the electrical conductivity of aqueous electrolytes. The conductivity is caused by electrical charge transport by mobile ions, and is explained by Coulomb's law. The electropotential established across the electrode array induces migration of the mobile ionic species associated with the contained material and pore water, resulting in a current.

It has been shown that for a given D.C. potential applied across a barrier, the amount of ion transport across the barrier (the current) is inversely proportional to the impermeability of the barrier. By measuring current and compensating for electrode chemistry, a precise and reproducible indication of barrier integrity can be accomplished.

A barrier medium which presents a high integrity will show a strong resistance to ionic transport. When an electropotential, such as a D.C. potential, is established across the electrodes little or no current will result. On the other hand, a barrier of lesser integrity will show a susceptibility to ion transport, and when the electropotential is applied a detectable current will result. The amount of current detected will provide an indication of the barrier's integrity. When the results are analyzed, the electrode spacing, the voltage applied, and the soil properties will all be taken into consideration. It also is noted that the foregoing process can be used to measure the relative impermeability of a barrier where no discrete leak or zone of discontinuity is involved.

In the event of a leak in the barrier, a specific anomaly in the ionic flux pattern within the barrier results. Such an anomaly gives rise to an electromagnetic flux field which is detectable with an appropriately designed electromagnetic sensor. This anomalous electromagnetic field can be used to precisely pinpoint the location of a leak in the barrier.

Referring now to FIG. 1, a geophysical barrier (1) surrounding a contaminated landfill or similar environmental isolation zone (2), is tested for integrity by the use of an array of cathode electrodes (3), which are electrically connected to an array of anode electrodes (4). One or more of the electrodes may comprise an ion exchange zone (8) as discussed in more detail below. An electrical potential is applied through means for establishing an electropotential (9); to the electrodes at a potential that is high enough to establish a significant ionic flux through the surrounding soil matrix. However, the intact geophysical barrier restricts such ionic transport (5). A subsequent breach in the barrier (6), permits an ion conductive pathway (7) across the barrier. This ionic flux can be sensed by an incidence of current detected via means for detecting current (10); which will predominate at the electrodes pair which is closest to the breach point. This apparatus may be used for long-term monitoring of the integrity of a geophysical barrier.

The apparatus may also comprise an electromagnetic sensor as discussed above, as well as a data acquisition station, and/or a data computer software system for data acquisition, analysis and graphical display. This instrumentation can measure the quantity of ions driven across the barrier by the electropotential gradient, and can be used to identify distorted electromagnetic fields, permitting the location of leakage zones in the geophysical barrier.

The area outside the barrier will generally contain clean soils and, optionally, a liquid suitable for conducting current, for example, a soil fertilizer solution. This soil fertilizer solution can be used to provide conductive ions, for example, hydrogen ions, to the system. The process also takes advantage of hydrogen ions which are generated by the oxidation of water at the anode and hydroxyl ions which are generated by the reduction of water at the cathode. Coupling solutions may also be used at the electrode to improve the overall performance of the process by specific electrode conditioning.

The electrode zones of the invention generally will be iso-potential areas which are established and maintained by an external power supply. The combination of anode electrode(s) and cathode electrode(s) will be referred to generally as an electrode pair. Electrodes are well known in the art and the choice of electrode will depend upon factors well known to skilled artisans. The use of electrodes discussed in co-pending application Ser. No. 08/084,065, which is incorporated by reference herein in its entirety, is expressly contemplated.

In an advantageous embodiment, one or more of the electrodes of the electrode pair may comprise a means for controlling the pH at the electrode. In particular, the electrode may comprise an ion exchange zone formed by ion exchange media surrounded by a hydrophobic barrier which substantially resists fouling and which is ion-permeable.

When ions reach the electrode as a result of the induced current, ions from the ion exchange zone may be released to control the pH at the electrode and to prevent the area surrounding the electrode from becoming too acidic or caustic. This control of chemistry around the electrode enhances the performance of the electrode, and of the process as a whole. Electrodes for use in this embodiment are described in further detail in co-pending application Ser. No. 08/234,458, which is incorporated by reference herein in its entirety.

The selection of an electromagnetic sensor with appropriate sensitivity is well within the skill of the art, as such sensors are well known. The sensor selection will, of course, depend upon field-dictated parameters. For example, sensors used with ice barriers will likely be different from sensors used with clay barriers. The electromagnetic sensor may be positioned outside of the barrier or inside the barrier, or may be moved along the outside or inside of the barrier. One or more electromagnetic sensors may be used.

In certain instances, the sensitivity of the process can be enhanced via the use of a high intensity and high frequency pulsed power system, such as a pulsed D.C. electropotential. This approach has been seen to take advantage of the inductance or capacitance properties of the contained material, thereby yielding an improvement in the ability of the process to locate a zone of intensified ion migration. Such an electropotential energy source also permits a wider spacing of both anode and cathode electrodes with little loss in sensitivity. The use of pulsed D.C. power can substantially enhance the sensitivity and/or cost effectiveness of this barrier detection method by providing an enhanced sensitivity to ions being driven by the electropotential force.

The natural diffusion of ions through a barrier also is considered. For example, it is recognized that the diffusion transport of impurity molecules such as NaCl through ice is in the range of $4 \times 10^{-13}$ meters$^2$/second. The natural diffusion of such impurities through a one meter section of ice will yield a contamination gradient of approximately $10^{-21}$ in 10,000 years. In general, such an extremely low diffusion coefficient can be considered to be "essentially zero". The imposition of an electrical potential in the range of 0.5 volts per cm will not cause any appreciable (or detectable) electrical current through such an ice barrier.

The migration of metal ions through a concrete barrier is another measure of the electrical resistance provided by a barrier. The diffusion coefficient of cobalt through concrete is reported to be $10^{-12}$ to $10^{-13}$ meters$^2$/second. It is obvious that this diffusion property of concrete is comparable to that of the ice barrier discussed above.

It can be seen that the transport of ionic species through such barriers is essentially zero and accordingly, even when a high voltage gradient is applied, there will be very minimal electrical current. The phrase "electrical conductivity is essentially zero" means that the geophysical barrier substantially resists any significant obstruction or blockage of ionic migration by the intact and continuous barrier. The operating efficiency includes the efficiency with which ions can pass through the barrier when being driven by the electropotential force. The term does not mean that the barrier will not permit a single ionic species to permeate, but rather that over an extended period of time the barrier will substantially resist the free ionic flux which would be associated with a natural soil zone.

The embodiments of the invention may be further illustrated through examples which show aspects of the invention in detail. These examples illustrate specific elements of the invention and are not to be construed as limiting the scope thereof.

EXAMPLE 1

An example of the use of electrical resistance measurements for measuring the integrity of a barrier can be seen with a barrier comprising frozen soil. Two bare electrodes are provided on opposite sides of a planned ice wall barrier. A D.C. potential is established across the barrier which causes an ionic transport while the subfreezing conditions are being established. When the barrier is frozen, ionic transport is not possible, and the detected current approaches zero.

EXAMPLE 2

This example was similar to Example 1, and demonstrated the measurement of the integrity of an ice wall barrier. The soil used in this experiment was a high clay content soil (nearly 20% clay) taken from a site near Oak Ridge, Tenn. The soil was compacted in a polyethylene container (of approximate 0.10 cubic meters) to a density that simulated the natural density. Contaminated soil pore water (simulant) was prepared containing 22,000 ppm sodium ion, and was used to dampen the soil. A liquid nitrogen coil was positioned within the soil mass so that a continuous wall of frozen soil could be established within the polyethylene barrier.

Two stainless steel rod type electrodes approximately 5 mm in diameter were placed on opposite sides of the planned ice wall barrier. The spacing between these electrodes was approximately 100 cm. The voltage applied was 50 volts D.C. Initially, the current was 150 milliamperes. After introduction of flow of liquid nitrogen, a complete freezing of the soil occurred within two hours. At this point, the current was essentially zero.

EXAMPLE 3

The same experimental setup was used as in Example 2, except that a heat trace wire was used to permit a leak to be maintained during the formation of the ice barrier. Using an array of ten thermocouples, it was possible to measure the relative proportions of melted soil (the leak area) to frozen soil. When the leak area was approximately 10 percent of the frozen soil, the current between the two electrodes was approximately 25 milliamperes.

It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. A process for determining the integrity of a geophysical barrier comprising the steps of:
   A) providing an electrode pair positioned on opposite sides of said barrier, wherein at least one electrode of said electrode pair comprises an ion exchange zone for controlling the pH at said electrode;
   B) establishing an electropotential across said electrode pair, and
   C) measuring the resultant current caused by said electropotential,
   wherein the magnitude of said current is inversely proportional to the integrity of said barrier.

2. A process according to claim 1, wherein said electropotential is a D.C. electropotential.

3. A process according to claim 2, wherein said D.C. electropotential is delivered in the form of intermittent pulses.

4. A process according to claim 3, wherein said pulses are short in duration.

5. A process according to claim 1, wherein said ion exchange zone is surrounded by a hydrophobic barrier which substantially resists fouling and which is ion-permeable.

6. A process according to claim 1, further comprising the step of measuring, with an electromagnetic sensor, any electromagnetic field caused by any anomaly in the ionic flux pattern of said current.

7. A process according to claim 6, wherein any leaks in said barrier are located by the detection of any distorted electromagnetic fields by said electromagnetic sensor.

8. An apparatus for determining the integrity of a geophysical barrier comprising:
   A) an electrode pair on opposite sides of said barrier, wherein at least one electrode of said electrode pair comprises an ion exchange zone for controlling the pH at said electrode,
   B) means for establishing an electropotential across said electrode pair, and
   C) means for detecting current across said barrier; wherein the magnitude of said current is inversely proportional to the integrity of said barrier.

9. The apparatus of claim 8, further comprising an electromagnetic sensor for measuring any electromagnetic field caused by any anomaly in the ionic flux pattern of said current.

10. The apparatus of claim 8, wherein said ion exchange zone is surrounded by a hydrophobic barrier which substantially resists fouling and which is ion-permeable.

* * * * *